United States Patent [19]

Pennev et al.

[11] Patent Number: 5,043,350

[45] Date of Patent: Aug. 27, 1991

[54] BENZO-FUSED CYCLOALKANE AND OXA- AND THIA-, CYCLOALKANE TRANS-1,2-DIAMINE DERIVATIVES

[75] Inventors: Penio Pennev, Chadds Ford, Pa.; Parthasarathi Rajagopalan; Richard M. Scribner, both of Wilmington, Del.

[73] Assignee: Du Pont Merck Pharmaceutical Company, Wilmington, Del.

[21] Appl. No.: 455,887

[22] Filed: Dec. 21, 1989

Related U.S. Application Data

[60] Division of Ser. No. 362,681, Jun. 7, 1989, which is a division of Ser. No. 71,028, Jul. 16, 1987, Pat. No. 4,876,269, which is a continuation-in-part of Ser. No. 905,543, Sep. 10, 1986, abandoned.

[51] Int. Cl.$^5$ ............... A61K 31/40; A61K 31/35; C07D 405/04; C07D 311/92
[52] U.S. Cl. .................. 514/428; 514/429; 514/454; 514/455; 548/525; 549/389
[58] Field of Search ............... 549/389; 514/454, 455, 514/428, 429; 548/525

[56] References Cited

U.S. PATENT DOCUMENTS

| | | | |
|---|---|---|---|
| 4,098,904 | 7/1978 | Szmuskovicz | 424/324 |
| 4,115,435 | 9/1978 | O'Brien et al. | 260/465.4 |
| 4,145,435 | 3/1979 | Szmuskovicz | 424/274 |
| 4,212,878 | 7/1980 | Lednicer et al. | 424/274 |
| 4,359,476 | 11/1982 | Kaplan et al. | 424/274 |
| 4,360,531 | 11/1982 | McMillan et al. | 424/274 |
| 4,438,130 | 3/1984 | Kaplan | 424/274 |
| 4,460,600 | 7/1984 | Kaplan | 424/274 |
| 4,466,977 | 8/1984 | McMillan et al. | 424/274 |
| 4,499,286 | 2/1985 | Binder | |
| 4,632,935 | 12/1986 | Kaplan | 514/429 |
| 4,656,182 | 4/1987 | Horwell | 514/324 |
| 4,663,343 | 5/1987 | Horwell et al. | 514/429 |
| 4,735,959 | 4/1988 | Grell et al. | |

FOREIGN PATENT DOCUMENTS

| | | |
|---|---|---|
| 108602 | 5/1984 | European Pat. Off. |
| 129991 | 1/1985 | European Pat. Off. |
| 147085 | 7/1985 | European Pat. Off. |

OTHER PUBLICATIONS

Martin, Pharmacol. Rev., vol. 19, pp. 463–521 (1967).
Martin, J. Pharmacol. Exp. Ther., vol. 197, pp. 517–532 (1976).
Von Voigtlander et al., J. Pharmcol. Exp. Ther., vol. 224, pp. 7–12 (1983).
Medicinal Chemistry, Burger (ed.), p. 42 (1960).

Primary Examiner—Robert A. Wax
Assistant Examiner—Fred Tsung

[57] ABSTRACT

Benzo-fused cycloalkane and oxa- and thia- cycloalkane trans-1,2-diamine compounds of the formula:

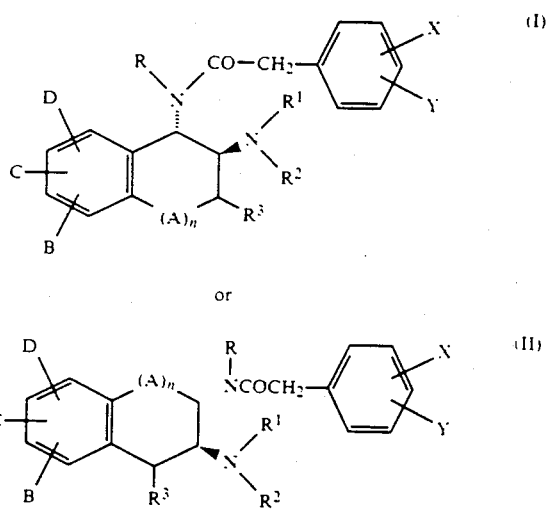

wherein A, B, C, D, n, X, Y, R, R$^1$, R$^2$ and R$^3$ are as defined in the specification, e.g., trans-3,4-dichloro-N-methyl-N-[2-(pyrrolidin-1-yl)-5-methoxy-1,2,3,4-tetrahydronaphth-1-yl]benzeneacetamide, and the pharmaceutically acceptable salts or N-oxides thereof, are useful as analgesics and/or diuretics.

21 Claims, No Drawings

BENZO-FUSED CYCLOALKANE AND OXA- AND THIA-, CYCLOALKANE TRANS-1,2-DIAMINE DERIVATIVES

This is a division of application Ser. No. 07/362,681, filed June 7, 1989, which is a division of application Ser. No. 07/071,028, filed July 16, 1987, now U.S. Pat. No. 4,876,269, issued Oct. 24, 1989, which in turn in a continuation-in-part of application Ser. No. 905,543, filed Sep. 10, 1986 (now abandoned).

FIELD OF THE INVENTION

The invention relates to benzo-fused cycloalkane compounds and their oxa- and thia- derivatives, processes for their preparation, pharmaceutical compositions containing them, and their use as analgesics and/or diuretics.

BACKGROUND OF THE INVENTION

Studies of the binding properties of opioid drugs and peptides at specific sites in the brain and other organs have suggested the existence of several types of opioid receptors. In the central nervous system (CNS), good evidence has been demonstrated for at least three categories of opioid receptors: $\mu$ (mu), k (kappa) and $\delta$ (delta). Nalorphine, W.R. Martin, *Pharmacol. Rev.*, 19, 463-521 (1967), and a series of benzomorphans, W.R. Martin, et al., *J. Pharmacol. Exp. Ther.*, 197, 517-532 (1976), were reported to display unusual pharmacological properties dissimilar to morphine, yet blocked by selective opioid antagonists. The existence of multiple subtypes of opioid receptors is of considerable interest as it suggests the possibility of separating the desirable (analgesic and psychotherapeutic) and the undesirable (abuse potential) effects of opioids.

Indeed, compounds that are agonists for k receptor have shown strong analgesia without opioid side effects such as dependence liability, respiratory depression, and constipation. The prototype of such compounds is U-50,488, trans-3,4-dichloro-N-methyl-N[2-(pyrrolidin-1-yl)cyclohexyl]benzeneacetamide, which is described in U.S. Pat. No. 4,115,435, and reported by P.F. VonVoigtlander, et al., *J. Pharmacol Exp. Ther.*, 224, 7 (1983). This compound is stated to exhibit analgesic actions in a variety of assays, such as thermal, pressure and irritant, in mice and rats.

Spirocyclic analogs of U-50,488 are disclosed in U.S. Pat. Nos. 4,359,476, 4,360,531, and 4,438,130, as analgesic compounds having low physical dependence liability in humans. Examples of these derivatives are trans-3,4-dichloro-N-methyl-N-[7-(pyrrolidin-1-yl)-1,4-dioxaspiro[4.5]dec-6-yl]benzeneacetamide; trans-3,4-dichloro-N-methyl-N-[7-(pyrrolidin-1-yl)-1,4-dioxaspiro[4.5]dec-8-yl]benzeneacetamide; and (±)-(5-a-7-a-,9β)-3,4-dichloro-N-methyl-N-[7-(pyrrolidin-1-yl)-1-oxaspiro[4.5]dec-8-yl]benzeneacetamide. Omega(Hydroxy-, Ether and Ester)-Alkyl-2-Amino-Cycloalkyl and Cycloalkenyl Amides active as analgesics are disclosed in U.S. Pat. No. 4,632,935.

Substituted trans-1,2-diaminocyclohexylamine compounds such as trans-N-methyl-N-[2-(1-pyrrolidinyl)cyclohexylbenzo[b]thiophene-4-acetamide are disclosed in U.S. Pat. No. 4,656,182. Napthaleneyloxy-1,2-diaminocyclohexyl amide compounds active as analgesics are disclosed in U.S. Pat. No. 4,663,343.

SUMMARY OF THE INVENTION

According to the present invention there is provided a compound having the formula:

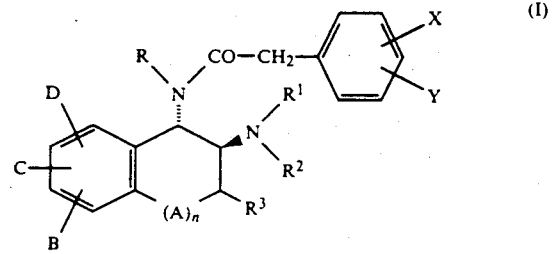

or

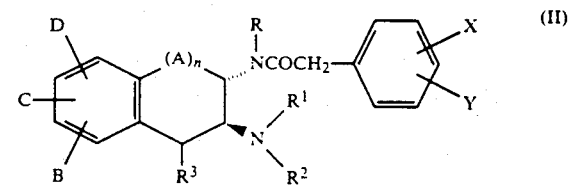

wherein for the enantiomers and racemic mixtures
n is 0 or 1;
A is

or, —CH$_2$CH$_2$— provided that in Formula (I), when n is 1, A may also be —O—, or —S—;
B, C and D independently are selected from the group consisting of H, OH, OCOR$^5$, OCH$_2$CH$_2$OR$^5$, OR$^6$, R$^6$, CH$_2$OR$^6$, CH$_2$COR$^7$, Cl, F, Br, I, NH$_2$, NHR$^8$, NR$^8$R$^9$, SH, SR$^6$, CH$_2$SR$^6$ and OC(S)N(CH$_3$)$_2$; or
two of B, C and D when on adjacent carbon atoms taken together form a fused benzo ring;
X and Y independently are selected from the group consisting of H, OCH$_3$, Cl, F, Br, I, NO$_2$, CF$_3$, CN, SO$_2$R$^{10}$, and SO$_2$CF$_3$; or
X and Y taken together with the benzene ring form

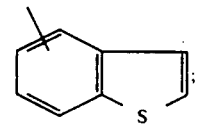

R and R$^1$ independently are selected from the group consisting of H, and alkyl of 1 to 3 carbon atoms;
R$^2$ is H; alkyl of 1 to 6 carbon atoms; CH$_2$CF$_3$; alkenylmethyl of 3 to 6 carbons atoms; hydroxyalkylmethyl of 2 to 5 carbon atoms; cycloalkyl of 3 to 6 carbon atoms; cyclopropylmethyl; cyclobutylmethyl, or phenylalkyl of 7 to 9 carbon atoms; or R$^2$ can be taken together with R$^1$ and the nitrogen to which they are attached to be 1-azetidinyl; 1-pyrrolidinyl optionally substituted at the 3-position by OH, alkyl of 1 to 3 carbon atoms, alkoxy of 1 to 3 carbon atoms or alkanoyloxy of 1 to 3 carbon atoms; 1-piperazinyl optionally substituted at the-4-position by alkyl of 1 to 3 carbon atoms; 1-morpholino; 2,5-dihydro-1H-pyrrol-1-yl; 3-azabicyclo[3.1.0]hexan-3-yl; or 3-azabicyclo[3.2.0]heptan-3-yl;

$R^3$ is H, but if n is 1 and A is $CH_2$, $R^3$ may also be $CH_3$, $CH_2OH$, CHO, or $COR^{11}$;

$R^4$ is H, alkyl of 1 to 6 carbon atoms, —$CH_2OH$—CHO, or $COR^{12}$;

$R^5$ is alkyl of 1 to 6 carbon atoms, phenyl, or monosubstituted phenyl;

$R^6$, $R^8$, $R^9$, $R^{10}$ and $R^{13}$ are independently an alkyl group of 1 to 3 carbon atoms; and $R^7$, $R^{11}$ and $R^{12}$ independently are selected from the group consisting of H, OH, $OR^{13}$, $NHR^{13}$, and or a stable N-oxide or a pharmaceutically acceptable salt thereof.

Also provided is a pharmaceutical composition consisting essentially of a pharmaceutically suitable carrier and an effective amount of at least one of the aforesaid compounds of Formula (I) or Formula (II).

Further provided is a method of treating pain in a mammal or a method of increasing the secretion of urine in a mammal comprising administering to the mammal an analgesic amount or a diuretic amount of at least one of the aforesaid compounds of Formula (I) or Formula (II).

Additionally provided is a process for preparing a compound of Formula (I) or Formula (II) comprising: reacting a compound of the formula:

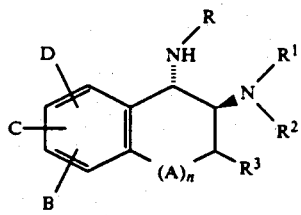

(VII)

or

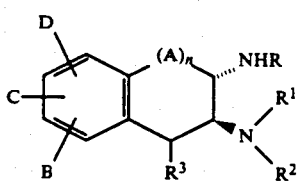

(XXI)

with (1) a carboxylic acid of the formula

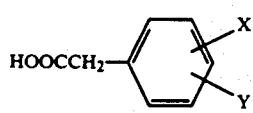

in the presence of dicyclohexylcarbodiimide;

(2) an acid chloride of the carboxylic acid in the presence of triethylamine, or aqueous sodium bicarbonate; or (3) an acyl imidazole prepared by reacting the carboxylic acid with carbonyl diimidazole.

PREFERRED EMBODIMENTS

Preferred compounds are those of Formula (I), particularly those having the formula

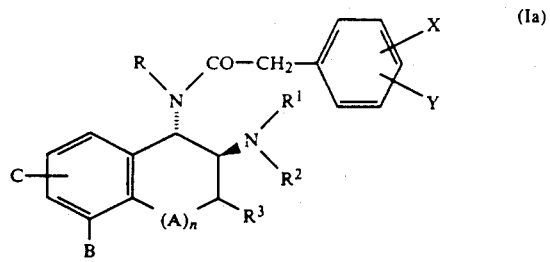

(Ia)

wherein
n is 1; or
A is —$CH_2$—, —O—, or —S—; or
B is OH, $OCOR^5$, $OCH_2CH_2OR^5$, $OR^6$, $CH_2OR^6$, or $CH_2COR^7$; or
C is H, OH, or $OR^6$; or
$R^1$ and $R^2$ independently are selected from H or alkyl of 1 to 3 carbon atoms or are taken together with the nitrogen to which they are attached to form the group 1-azetidinyl, 1-pyrrolidinyl, 1-(2,5-dihydro-1H-pyrrolyl) or 1-piperidinyl.

More preferred are compounds of Formula (Ia) wherein A is —$CH_2$—.

Specifically preferred compounds include:
(1) trans-3,4-dichloro-N-methyl-N-2-(pyrrolidin-1-yl)-5-methoxy-1,2,3,4-tetrahydronaphth-1-yl]benzeneacetamide hydrochloride or the methansulfonic acid salt;

(2) trans-3,4-dichloro-N-methyl-N-[2-(pyrrolidin-1-yl)-1,2,3,4-tetrahydronaphth-1-yl]benzeneacetamide hydrochloride;

(3) trans-3,4-dichloro-N-methyl-N-2-(pyrrolidin-1-yl)-6-methoxy-1,2,3,4-tetrahydronaphth-1-yl]benzeneacetamide hydrochloride;

(4) trans-3,4-dichloro-N-methyl-N-2-(pyrrolidin-1-yl)-6-hydroxy-1,2,3,4-tetrahydronaphth-1-yl]benzeneacetamide hydrochloride;

(5) (+) trans-3,4-dichloro-N-methyl-N-2-(pyrrolidin-1-yl)-1,2,3,4-tetrahydronaphth-1-yl]benzeneacetamide hydrochloride;

(6) trans-3,4-dichloro-N-methyl-N-[2,3-dihydro-2-(pyrrolidin-1-yl)-1H-inden-1-yl]benzeneacetamidehydrochloride;

(7) trans-3,4-dichloro-N-methyl-N-[3,4-dihydro-3-(pyrrolidin-1-yl)-2H-benzopyran-4-1]benzeneacetamide hydrochloride;

(8) trans-3,4-dichloro-N-methyl-N-[2-(pyrro-lidin-1-yl)-5-hydroxy-1,2,3,4-tetrahydronaphth-1-yl]benzeneacetamide hydrochloride;

(9) trans-3,4-dichloro-N-methyl-N-[2-(pyrrolidin-1-etrahydronaphth-1-yl)-5-propionyloxy-1,2,3,4 -tetrahydronaphth-1-yl]benzeneacetamide hydrochloride;

(10) trans-3,4-dichloro-N-methyl-N-[2-(pyrrolidin-1-yl)-5-benzoyloxy-1,2,3,4-tetrahydronaphth-1yl]benzeneacetamide hydrochloride;

(11) trans-3,4-dichloro-N-methyl-N-[2-(pyrrolidin-1-yl)-6,7-dihydroxy-1,2,3,4-tetrahydronaphth-1yl]benzeneacetamide hydrochloride;

(12) trans-N-methyl-N-[3,4-dihydro-3-(pyrrolidin-1-yl)-2H-benzopyran-4-yl]benzeneacetamide hydrochloride;

(13) trans-3,4-dichloro-N-methyl-N-[3,4-dihydro-8-methoxy-3-(pyrrolidin-1-yl)-2H-benzopyran-4yl]benzeneacetamide hydrochloride;

(14) trans-3,4-dichloro-N-methyl-N-[2-(pyrrolidin-1-yl)-5-(N,N-dimethylthiocarbamoyloxy)-1,2,3,4-tetrahydronaphth-1-yl]benzeneacetamide hydrochloride; and

(15) trans-3,4-dichloro-N-methyl-N-[2-(2,5-dihydro-1H-pyrrol-1-yl)-5-methoxy-1,2,3,4-tetrahydronaphth-1-yl]benzeneacetamide hydrochloride.

DETAILED DESCRIPTION OF THE INVENTION

Methods for the synthesis of the compounds of the invention are illustrated in Schemes 1 and 2.

The starting compounds of Formula III and IX can be prepared either according to literature procedures or by modifications to these procedures which should be apparent to those familiar with the art of organic synthesis. A convenient way to prepare the starting olefin III is by reduction of the corresponding ketone (e.g., 1-tetralone) to the corresponding alcohol (e.g., 1-tetralol) followed by dehydration of the alcohol (e.g., to 1,2-dihydronaphthalene). Dehydration of the alcohol can be done by heating in the presence of acid (e.g., $KHSO_4$), pyrolysis of the alcohol acetate, or often most conveniently by simply heating its solution in DMSO at 100–200° C., the preferred temperature depending on the nature of $R^3$, $(A)_n$, B, C, and D. Some references that describe the preparation of olefins III or their precursor ketones or alcohols include: *J. Chem. Soc.*, 4425 (1961); *J. Chem. Soc. Chem. Commun.*, 453 (1984); *Chem. Pharm. Bull.*, 25(4), 632 (1977); *J. Chem. Soc.*, 3271 (1949); *ibid*, 1894 (1953); *Chem. Pharm. Bull.*, 26, 394, 1511 (1978); *J. Med. Chem.*, 28, 1398 (1985); *ibid* 12, 487 (1969); U.S. Pat. No. 4,448,990 (1984); *Chem. Pharm. Bull.*, 25 (11) 2988, 3066 (1977); *ibid* 25(12) 3289 (1977); *ibid* 31 (7) 2329 (1983); *ibid* 32(1) 130 (1984); *Bull Chem. Soc. Japan*, 52, 251 (1979); *J. Chem. Soc. Chem. Comm.*, 63 (1976); *J. Indian Chem. Soc.*, LX, 1163 (1983); *J. Med. Chem.*, 15, 1306 (1972); U.S. Pat. No. 3,379,731 (1968); *J. Org. Chem.*, 37(1), 13 (1972). This list is intended to be illustrative, not comprehensive.

According to Scheme 1, a compound of Formula III can be converted into an epoxide of Formula IV by a peracid such as 3-chloroperbenzoic acid in a halogenated solvent such as methylene chloride at a temperature between 0° and 25° C. Alternatively, the epoxide of Formula IV can be prepared by converting a compound of Formula III into a bromohydrin of Formula V with N-bromosuccinimide in a water-organic solvent mixture such as aqueous dimethylsulfoxide at room temperature followed by treating the compound of Formula V with a strong base such as sodium hydroxide in a solvent such as aqueous dioxane at room temperature.

An epoxide of Formula IV, on treatment with an amine, $R^1NHR^2$, preferably in the presence of a polar solvent such as ethanol or water at a temperature between 25° and 80° C., yields an amino alcohol of Formula VI. Alternatively, a compound of Formula VI can also be obtained directly from a bromohydrin V by treating with an amine, $R^1NHR^2$. Route V→VI is sometimes referred to route IV→VI when B, C, and D are electron-donating groups, such as $OCH_3$.

An aminoalcohol of Formula VI is converted to a diamine of Formula VII by first reacting with methanesulfonyl chloride in a chlorinated solvent such as methylene chloride in the presence of a base such as triethylamine at a temperature between 0° and 5° C. Further treatment of the resulting sulfonate with an excess of an alcoholic solution of an amine, $RNH_2$, such as methylamine, ethylamine, or n-propylamine, at a temperature between 70° and 80° C. yields a compound of Formula VII. Alternatively, an aminoalcohol of Formula VI can be treated with chlorosulfonic acid in a chlorinated solvent such as methylene chloride at a temperature between 0° and 25° C. to afford the sulfate salt of a compound of Formula VIII which on treatment with an amine $RNH_2$ affords a diamine of Formula VII.

A diamine of Formula VII is converted to a compound of Formula (I) by conventional methods, e.g., treatment with a carboxylic acid ($ArCH_2COOH$) either as its acid chloride in the presence of triethylamine, or aqueous sodium bicarbonate, or as its acyl imidazole prepared by reacting the acid with carbonyl diimidazole, or with the acid itself in the presence of dicyclohexylcarbodiimide.

SCHEME 1

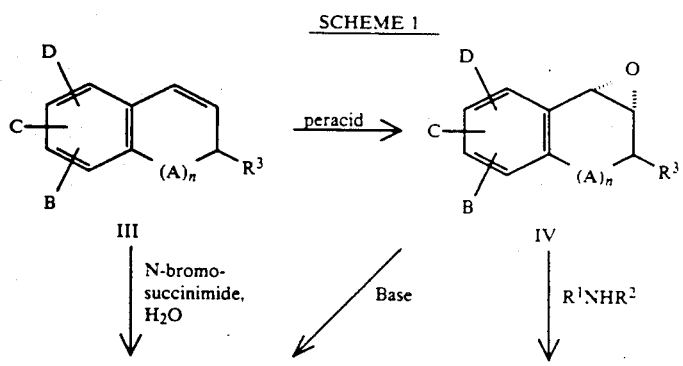

SCHEME 1

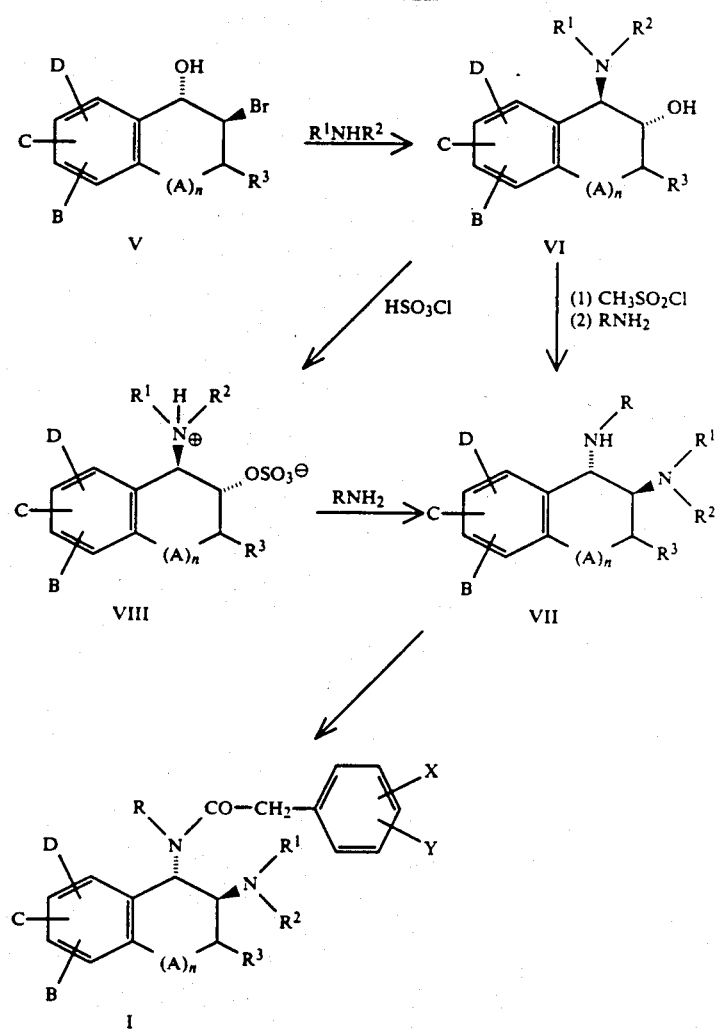

As shown in Scheme 2, the compounds of the invention can be prepared by converting a ketone of Formula IX to an oximino derivative of Formula X, using n-butyl nitrite and a strong base such as sodium methoxide, or sodium hydroxide, in a polar solvent such as ethanol at a temperature between 0° and 5° C. The oximino compound of Formula X is then reduced with hydrogen in the presence of a catalyst such as palladium on carbon in a polar solvent such as ethanol containing a stoichiometric amount of an inorganic acid such as hydrochloric acid to yield an amino ketone of Formula XI which can be further reduced to a transamino alcohol of Formula XV with a borohydride reducing agent such as sodium borohydride in a polar solvent such as aqueous ethanol at a temperature between 0° and 25° C. The amino alcohol can be converted into a compound of Formula XVI via N-alkylation reactions that have been described in the literature, e.g., J. March, "Advanced Organic Chemistry", Wiley Interscience, New York, N.Y.

Transformation of a compound of Formula XVI to a diamine of Formula VII can be achieved in the same manner as converting an amino alcohol of Formula VI into a diamine of Formula VII as shown in Scheme 1.

Alternatively, an amino ketone of Formula XI can be converted to an amide of Formula XII by employing N-acylation reactions known to one skilled in the art such as using an acid chloride. The resulting amide can be reduced to a cis-amino alcohol of Formula XIII with a reducing agent such as lithium aluminum hydride (LAH) in an inert solvent such as tetrahydrofuran at a temperature between 25° and 80° C. An N-alkylation reaction is employed to convert an amino alcohol of Formula XIII to a compound of Formula XIV which is then treated with methanesulfonyl chloride in a chlorinated solvent such as methylene chloride at a temperature between 0° and 5° C. followed by an alcoholic solution of amine $RNH_2$ at a temperature between 75° and 80° C. to give a compound of Formula VII.

The diamines of Formula VII are converted to Formula (I) compounds of the invention by methods described in Scheme 1.

SCHEME 2

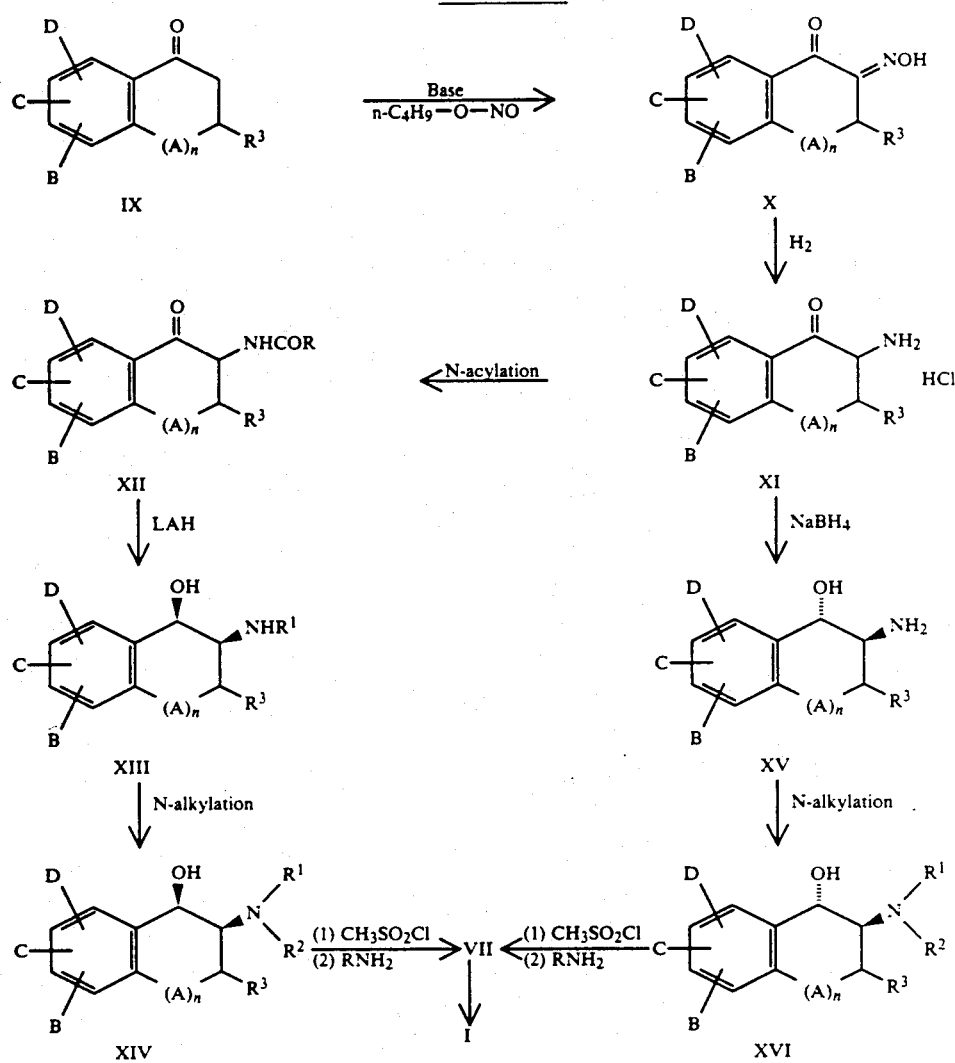

Schemes 1 and 2 leading to compounds of Formula (I) are equally applicable to the preparation of compounds of Formula (II). This analogous synthetic sequence is summarized in Scheme 3. Some of the intermediates in Scheme 3 may be accompanied by regioisomers. The undesirable isomers can be removed by conventional methods of separation, e.g., chromatography such as high pressure liquid chromatography (HPLC), thin layer chromatography (TLC), etc., distillation, or fractional crystallization.

SCHEME 3

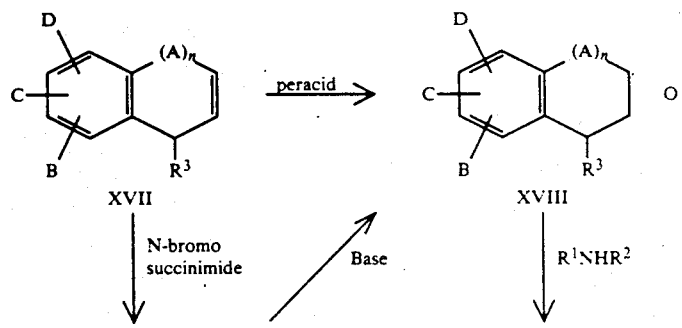

SCHEME 3

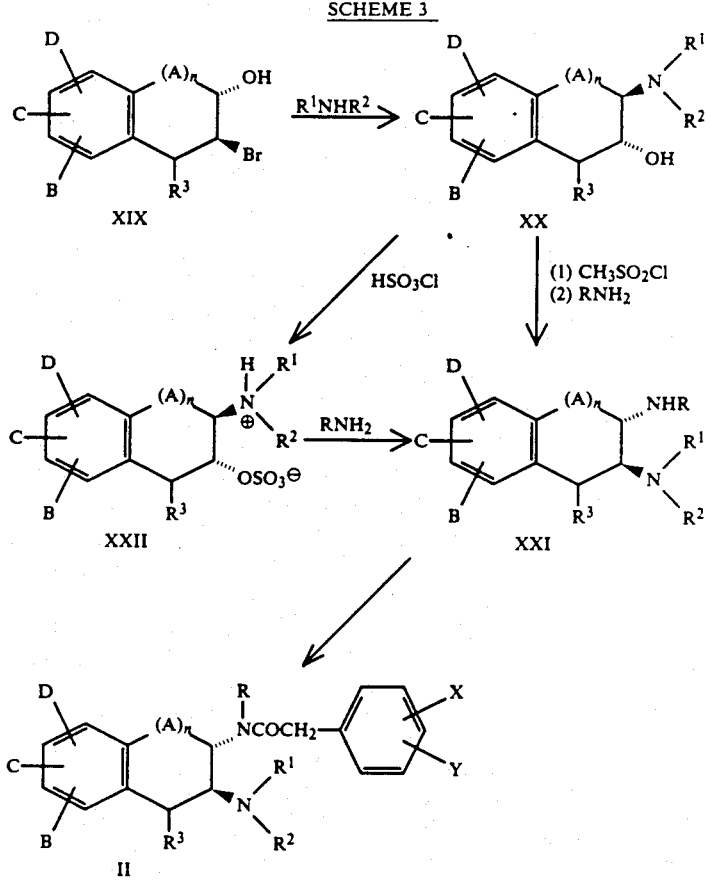

Where several alternative routes are outlined in Schemes 1, 2, and 3, sometimes one synthetic route can be preferred over another, depending on the particular compounds involved. One skilled in the art of organic synthesis can choose the best route.

In Schemes 1, 2, and 3, intermediates and products are written to show what is intended to be the stereochemical relationships (e.g. cis and trans relationships). However, these structures in most cases are intended to represent d,l (racemic) forms, and not absolute stereochemical configurations. This is not to imply, however, that enantiomerically pure (resolved) compounds are not sometimes the preferred Compounds of the invention.

Whereas the Schemes 1, 2, and 3 outline the most general routes to the compounds of the invention, it will be understood by one skilled in the art of organic synthesis that these schemes do not include every possible approach to preparing compounds of Formula (I) or Formula (II). For example, for some definitions of groups B, C, and D, it may be preferable to start the reaction sequence from a starting material (a compound of Formula III, IX, or XVII) where the B, C, or D groups are precursors to the eventually desired groups. Thus, B may be nitro or acetamido and later in the sequence it may be reduced to $NH_2$ or $NHC_2H_5$. The sequence may also start from compounds of Formula III, IX, or XVII where B, C, or D are methoxy and are to be demethylated later, e.g., at the end of the sequence, to the corresponding phenol. Often it is convenient to start with $R^3$ being a carboxylic ester, e.g., a tertiary-butylcarboxylic ester, and then at the end of the synthesis, to hydrolyze and reduce the ester group to $CH_2OH$ or CHO; or to hydrolyze and react the ester with an appropriate organometallic reagent such as methyl lithium to afford $COR^{11}$. Such ramifications of the basic schemes are common practice in analoging compounds of pharmaceutical interest.

Pharmaceutically acceptable acid addition salts of amines I or II can be prepared by reacting the free bases I or II with a stoichiometric amount of an appropriate acid such as hydrogen chloride, hydrogen bromide, hydrogen iodide, phosphoric acid, sulfuric acid, acetic acid, lactic acid, maleic acid, fumaric acid, succinic acid, citric acid, benzoic acid, salicylic acid, pamoic acid, methanesulfonic acid, naphthalenesulfonic acid, p-toluenesulfonic acid and the like. The reaction can be carried out in water or in an organic solvent, or a mixture of the two; but nonaqueous media like ether, ethyl acetate, ethanol, isopropanol, or acetonitrile are generally preferred. Optically resolved enantiomers usually are conveniently prepared from optically active acids such as (+) or (−) tartaric acid or dibenzoyltartaric acid, or citric acid, or the like. One enantiomer may be more active than the other.

Amine oxides of amines I or II can be prepared in the generally same manner as other amine oxides, for example, by reaction of the amines with hydrogen peroxide or peracetic acid in an aqueous medium, or by reaction with a peracid such as peracetic acid or m-chloroperbenzoic acid in a nonaqueous medium such as methylene chloride. The amine oxides are separated from acidic reaction products by chromatography, e.g., on basic alumina, or by treatment with aqueous base such as sodium bicarbonate.

The invention can be further understood by the examples in which parts and percentages are by weight unless otherwise indicated and all temperatures are in degrees centigrade. The compounds were analyzed by proton nmr, TLC, mass spectroscopy, and by elemental analysis (C,H,N).

EXAMPLE 1 trans-3,4-Dichloro-N-methyl-N-[2-(pyrrolidin-1-yl)-5-methoxy-1,2,3,4-tetrahydronaphth-l-yl]benzeneacetamide and its hydrochloride salt Step 1: 5-Methoxy-1-tetralol To a round bottom flask (1 liter) was added 5-methoxy-1-tetralone (100 g, 0.57 mole). Ethanol (400 ml) was added and the resultant suspension was stirred at room temperature. Sodium borohydride (17 g, 0.45 mole) was added in portions over a period of about 20 minutes. When the reaction mixture became warm (about 40° C.), it was cooled briefly in an ice/—$H_2O$ bath to bring the temperature to approximately room temperature. The resulting clear solution was stirred for 4–5 hours after the addition was completed, and then about 1/2 of the ethanol was evaporated under reduced pressure on a rotating evaporator. The remaining mixture was mixed with water (about 1.5 l) and extracted (3 times) with ethyl acetate. The ethyl acetate extracts were combined and washed with water (2 times), washed with saturated NaCl, dried over $MgSO_4$, and evaporated, to give 5-methoxy-1-tetralol (about 100 g), m.p. 75°–76°; TLC (2:1 EtOAc/hex) $R_f=0.6$; 1 spot. IR showed no C=0 peak.

Step 2: 8-Methoxy-1,2-dihydronaphthalene

The above product (about 100 g) in dimethylsulfoxide (DMSO, 350 ml) was heated in an oil bath at 170° with stirring for 12 hours. The mixture was cooled to room temperature and poured into $H_2O$ (3 l). The water/DMSO mixture was extracted with ether (3 times). The ether layers were combined and washed with water (2 times), washed with saturated NaCl (1 time), and dried over anhyd. $K_2CO_3$. The ether was evaporated and the remaining liquid was distilled bulb to bulb to give 8-methoxy-1,2-dihydronaphthalene (about 80 g), b.p. about 117°–123°/4.5–5 mm; TLC: $R_f=0.8$ (1:1 ether/hexane)

Step 3: 1,2-Epoxy-5-methoxy-1,2,3,4-tetrahydronaphthalene

A solution of the above product (80 g, 0.5 mole) in $CH_2Cl_2$ (300 ml) was stirred in a 5 liter 3-neck round-bottom flask at 0–3° (ice/salt bath). A solution of 3-chloroperoxybenzoic acid (97 g, 0.50 mole of 85% pure) in $CH_2Cl_2$ (2 l) was added dropwise with cooling over a 3 hour period (ca. 13 ml/min.) and then, with continued cooling, the mixture was stirred for 3 more hours at 0°. To the cold reaction mixture was then added with stirring 10% $Na_2CO_3$ aqueous solution (750 ml). The mixture was transferred to a separatory funnel, and the lower $CH_2Cl_2$ layer was drawn off. The $CH_2Cl_2$ layer was washed with 10% $Na_2CO_3$ aqueous solution (2×75 ml) and once with water. The $CH_2Cl_2$ solution was tested with moist starch/iodide test paper for the absence of peroxide. The solution was dried over $MgSO_4$ and evaporated at 45° to give 1,2-epoxy-5-methoxy-1,2,3,4-tetrahydronaphthalene (95 g).

Step 4: trans-1-(Pyrrolidin-1-yl)-2-hydroxy-5-methoxy-1,2,3,4-trahydronaphthalene To a flask containing the above epoxide (17.6 g, 0.1 mole) was added dropwise, with stirring over a period of about 10 minutes, pyrrolidine (10 ml, 0.12 mole) in ethanol (5 ml). The mixture was stirred at room temperature for about 18 hours and then warmed at 50° for about 1 hour. On cooling, the solid was collected by filtration and recrystallized from absolute ethanol. The crystalline product, trans-1-(pyrrolidin-I-yl)-2-hydroxy-5-methoxy-1,2,3,4tetrahydronaphthalene, (14.5 g, ~59% yield) was collected by filtration, washed with cold ethanol, and air dried, m.p. 113–115° C.; TLC $R_f=0.33$ (2:1 EtOAc/hexane).

Step 5: trans-1-(pyrrolidin-1-yl)-2-hydroxy-5-methoxy-1,2,3,4-tetrahydronaphthalene-0-sulfonic acid A solution of the above pyrrolidinyl alcohol (47 g, 0.19 mole) in $CH_2Cl_2$ (250 ml) was stirred under $N_2$ and cooled in an ice-salt bath while chlorosulfonic acid (12.7 ml, 22.2 g, 0.19 mole) in $CH_2Cl_2$ (250 ml) was added dropwise. When addition was complete, the mixture was stirred at 0–5° for 2 hours and then at room temperature overnight. The solid was collected by filtration and air dried, giving trans-1-(pyrrolidin-1-yl)-2-hydroxy-5-methoxy-1,2,3,4-tetrahydronaphthalene-O-sulfonic acid (62 g, 100%), m.p (dec.).

Step 6: trans-1-Methylamino-5-methoxy-2-(pyrrolidin-1-yl)-1,2, 3,4-tetrahydronaphthalene A Parr hydrogenation bottle was loaded with the above dry sulfonate salt (62 g, 0.19 mole) and 33% $CH_3NH_2$/EtOH (120 ml, 1 mole). The bottle was sealed with a rubber stopper held in place by a clamp and the contents were heated in an oil bath at 70° for 20 hours with stirring. The mixture was cooled to room temperature and evaporated on a rotating evaporator to remove most of the ethanol. Ethyl acetate was added to the residual material followed by 5% NaOH aqueous solution (100 ml). The ethyl acetate layer was removed and the aqueous phase was extracted with ethyl acetate. The organic extracts were dried over $K_2CO_3$. Evaporation of the solvent gave crude diamine free base, trans-1-methylamino-5-methoxy-2-(pyrrolidin-1-yl)-1,2,3,4-tetrahydronaphthalene (49 g).

This free base was dissolved in toluene and the solution was evaporated before the next step to remove traces of water or ethanol. This diamine can also be prepared by reacting trans-1-(pyrrolidin-1-yl)-2-hydroxy-5-methoxy-1,2,3,4-tetrahydronaphthalene with methanesulfonyl chloride in the presence of triethylamine followed by treatment of the methanesulfonate with methylamine using a procedure analogous to that used in Example 2, step 2.

Step 7: trans-3,4-Dichloro-N-methyl-N-[2-(pyrrolidin-1-yl)-5-methoxy-1,2,3,4-tetrahydronaphth-1-yl]benzene acetamide To a solution of 3,4-dichlorophenylacetic acid (51.6 g, 0.25 mole) in dry tetrahydrofuran (THF) (300 ml) under $N_2$ was added with stirring 1,1-carbonyldiimidazole (40.8 g, 0.25 mole). The reaction mixture was stirred for 2 hours at room temperature and then a solution of diamine from Step 6 (54.6 g, 0.21 mole) in dry THF (110 ml) was added dropwise. The mixture was stirred overnight at room temperature under $N_2$. The solvent was then evaporated in vacuo. The residue was dissolved in ether (1 l) and the solution washed with 5% NaOH aqueous solution (2×250 ml), then water, dried over MgS04, and evaporated, giving trans-3,4-dichloro-N-methyl-N-[2-(pyrrolidin-1-yl)-5-methoxy-1,2,3,4-tetrahydronaphth-1-yl]benzene (89 g).

Step 8: trans-3,4-Dichloro-N-methyl-N-[2-pyrrolidin-1-yl)-5-methoxy-1,2,3,4-tetrahydronaphth-1-yl]benzene-acetamide hydrochloride The above crude amine amide (free base, 89 g), was dissolved in THF (400 ml) and this solution was added to ether (1 l) containing dissolved gaseous HCl to precipitate a gummy HCl salt. Ether (500 ml) was added to the mixture and the gum was triturated. The liquid was decanted and fresh ether (700 ml) was added to give a solid. The ether was decanted and acetone (400 ml) was added to the solid. The acetone mixture was boiled for 10-15 minutes, kept at room temperature for 1-1.5 hours, and filtered to collect the solid HCl salt (32 g). Recrystallization from isopropanol/methanol (1:1, 400 ml) using decolorizing charcoal, gave on standing overnight at room temperature, trans-3,4-dichloro-N-methyl-N-[2-(pyrrolidin-1-yl)-5-methoxy-1,2,3,4-tetrahydronaphth-1-yl]hydrochloride as white crystals (21.6 g), m.p. 230-232° (dec). The acetone filtrate (from which 32 g of crude product had been isolated) was evaporated to give an oil (55 g). Boiling of the residual oil with fresh acetone and then evaporation of the acetone on the rotating evaporator was repeated three times to remove traces of solvent and then the product was crystallized from isopropanol and acetone giving a second crop (about 9 g), m.p. 225-227°. A smaller 3rd crop can sometimes be isolated.

EXAMPLE 2 trans-3,4-Dichloro-N-methyl-N-[2-(pyrrolidin-1-yl)-1,2,3,4-tetrahydronaphth-1-yl]benzeneacetamide hydrochloride Step 1: trans-1,2,3,4-tetrahydro-2-hydroxy-1-(pyrrolidin-1-yl)naphthalene A mixture of 1,2-epoxy-1,2,3,4-tetrahydro-naphthalene (19.8 g), pyrrolidine (15 ml) and ethanol (75 ml) was stirred at reflux for 2 hours and evaporated of the volatiles under reduced pressure. The residue was dissolved in ether and the solution was extracted with 1N hydrochloric acid (200 ml). The acid extract was washed with ether and basified with 1N sodium hydroxide aqueous solution with cooling. The mixture was extracted with ether (2X) and the combined ether extracts were washed with water, dried over magnesium sulfate and evaporated under reduced pressure. The residual viscous liquid was distilled under vacuum to yield trans-1,2,3,4-tetrahydro-2-hydroxy-1-(pyrrolidin-1-yl)naphthalene (16.5 g), b.p. 128-135°/0.25 torr.

Step 2: trans-1,2,3,4-tetrahydro-1-methylamino-2-(pyrrolidin-1-yl)naphthalene

A solution of methanesulfonyl chloride (10.3 g) in methylene chloride (50 ml) was added rapidly .in drops to a stirred and cooled (0.5° C.) solution of trans-1,2,3,4-tetrahydro-2-hydroxy-1-(pyrrolidin-1-yl)naphthalene (10.3 g) and triethylamine (10 g) in methylene chloride (100 ml). After the addition was complete, the mixture was stirred at room temperature for 3 hours and then evaporated under reduced pressure. The residue was treated carefully with a 33% solution of methylamine in ethanol (125 ml) and the mixture was stirred at reflux for 2 hours followed by evaporation of the solvent under reduced pressure. The residue was treated with water and extracted twice with ether. The combined ether extracts were washed with 2N sodium hydroxide and then with water, dried over magnesium sulfate and evaporated under reduced pressure. The residual viscous liquid was distilled under vacuum to yield trans-1,2,3,4-tetrahydro-1-methylamino-2-(pyrrolidin-1-yl)naphthalene (6.2 g), b.p. 126-134° /0.25 torr.

Step 3: trans-3,4-Dichloro-N-methyl-N-[2-(pyrrolidin-1-yl)-1,2,3,4-tetrahydronaphth-1-yl]benzeneacetamide hydrochloride A solution of dichlorophenylacetyl chloride (1.1 g) in methylene chloride (25 ml) was added to a solution of the above diamine (1.1 g) in methylene chloride (50 ml) and the solution was stirred with aqueous sodium bicarbonate (75 ml) for 2 hours at room temperature. The organic layer was separated and washed with aqueous sodium carbonate and then with water, dried ($MgSO_4$) and evaporated, to yield an oil (1.5 g) of the crude title compound. This oil was dissolved in THF and added to a solution of HCl in ether. The hydrochloride salt that precipitated was washed with ether and air dried. The crude salt was crystallized from acetone. Recrystallization from isopropanol gave the pure hydrochloride salt of the title compound, m.p. 232-234° (dec).

This procedure exemplifies the use of an alternate synthetic route to compounds of this invention. (Scheme I, IV→VI→VIII→VII→I).

EXAMPLE 3 trans-3,4-Dichloro-N-methyl-N-[2-(pyrrolidin-1-yl)-6-methoxy-1,2,3,4-tetrahydronaphth-1-yl]-benzeneacetamide and its hydrochloride salt Step 1: trans-2-Bromo-1-hydroxy-6-methoxy-1,2,3,4tetrahydronaphthalene To a solution of 6-methoxy-1,2-dihydronaphthalene (44.8 g, 0.28 mole) dissolved in DMSO (450 ml) was added with stirring $H_2O$ (16 ml). To the stirred mixture was added in 5 portions, N-bromosuccinimide (99.7 g, 0.56 mole) while the exotherm was controlled by an ice bath. The mixture was stirred at room temperature for 3 hours. Water (ca. 1 l.) was added and the mixture was extracted with ether (3 times). The combined extracts were washed with water twice, then with 5% $NaHCO_3$, dried over $K_2CO_3$, filtered, and evaporated to give an oil. After all the solvent had been removed, the oil crystallized on being scratched. It was recrystallized from hexane/ethyl acetate to yield trans-2-bromo-1-hydroxy-6-methoxy-1,2,3,4-tetrahydronaphthalene, m.p. 80-82°, $R_f=0.85$, silica gel, EtOAc; second crop from filtrate, 13 g, m.p. 80-81°.

Step 2: trans-2-hydroxy-1-(pyrrolidin-1-yl)-6-methoxy-1,2,3,4-tetrahydronaphth

To the above bromohydrin (30.8 g, 0.12 mole), cooled in a water bath, was added pyrrolidine (240 ml) and water (47 ml) all at once. The mixture was cooled for 10 minutes and then allowed to stand at room temperature for 22 hours. The excess pyrrolidine was evaporated on a rotating evaporator. Aqueous 10% $Na_2CO_3$ was added and the mixture was extracted with ethyl acetate (3x). The extract was dried over $MgSO_4$ and evaporated, giving trans-2-hydroxy-1-(pyrrolidin-1-yl)-6-methoxy-1,2,3,4-tetrahydro-naphthalene which was crystallized from isopropanol. First crop, 17 g (m.p. 9-80°), second crop 7 g (m.p. 78-79°).

Step 3: trans-2-Hydroxy-1-(pyrrolidin-1-yl)-6-methoxy-1,2,3,4-tetrahydronaphth-0-sulfonic acid A solution of the above amino alcohol (7.4 g, 30 mmoles) in methylene chloride (30 ml) was cooled in ice while a solution of chlorosulfonic acid (2 ml) in methylene chloride (60 ml) was added dropwise. The mixture was stirred under nitrogen for 2 hours with cooling and then at room temperature overnight. The white precipitate was collected by filtration, washed twice with fresh methylene chloride, and dried to give trans-2-hydroxy- 1-(pyrrolidin-1-yl)-6-methoxy-1,2,3,4-tetrahydronaphth O-sulfonic acid (8.7 g), m.p. 210-212° (dec).

Step 4: trans-1-methylamino-2-(pyrrolidin-1-yl)-6-methoxy-1,2,3,4-tetrahydronaphth The above 0-sulfonic acid salt (8.6 g) and 30% methylamine in ethanol (20 ml) were heated in a sealed Parr bottle at 50° for 3-4 hours and then at 70° overnight. The mixture was evaporated in vacuo and ethyl acetate was added to the residue. Aqueous 5% sodium hydroxide was added, and the mixture was extracted quickly with ethyl acetate (3x). The ethyl acetate extract was dried over anhydrous potassium carbonate and then evaporated, giving trans-1-methylamino-2-(pyrrolidin-1-yl)-6-methoxy-1,2,3,4-tetrahydronaphth (3.5 g) as an oil. The aqueous layer was further extracted with methylene chloride, giving an additional amount of the product (0.5 g).

Step 5: trans-3,4-Dichloro-N-methyl-N-[2-(pyrrolidin-yl)-6-methoxy-1,2,3,4-tetrahydro-1-yl]benzeneacetamide hydrochloride The above diamine was converted into the corresponding 3,4-dichlorobenzeneacetamide by the action of 3,4-dichlorophenylacetic acid (3.37 g) that had been treated with N,N,-carbonyldiimidazole (2.6 g) in THF by a procedure similar to that used in Example 1, step 7.

This gave an amino amide that was converted to its hydrochloride salt (by the procedure described in Example 1, step 8) which was recrystallized from isopropanol/methanol. The salt was washed with acetone and recrystallized from isopropanol/methanol again for an analytical sample of trans-3,4-dichloro-N-methyl N-2-(pyrrolidin-1-yl)-6-methoxy-1,2,3,4-tetrahydro-1yl]benzeneacetamide hydrochloride, m.p. 245-247° (dec.).

EXAMPLE 4 trans-3,4-Dichloro-N-methyl-N-[2-(pyrrolidin-1-yl)-6-hydroxy-1,2,3,4-tetrahydro-1-yl]benzeneacetamide hydrochloride trans-3,4-Dichloro-N-methyl-N-[2-pyrro-lidin-1-yl)-6-methoxy-1,2,3,4-tetrahydro-1-yl]benzeneacetamide was treated with 6 molar equivalents of boron tribromide in $CH_2Cl_2$ at −78°. The reaction mixture was allowed to warm slowly to room temperature and stirred at room temperature for 2 hrs. The reaction mixture was then treated with methanol and then aqueous 5% $NaHCO_3$. Extraction with $CH_2Cl_2$ gave the free base form of the desired product. The free base was dissolved in tetrahydrofuran and treated with HCl/ether, giving the title compound, m.p. 238-240°.

EXAMPLE 5

A. (+) trans-3,4-Dichloro-N-methyl-N-[2-(pyrrolidin-1-yl)-1,2,3,4-tetrahydronaphthyl]benzeneacetamide and its hydrochloride salt The compound (d,1) 3,4-dichloro-N-methyl-N-[2-(pyrrolidin-1-yl)-1,2,3,4-tetrahydronaphth-1-yl]benzeneacetamide hydrochloride prepared as in Example 2 was converted to its free base with aqueous potassium carbonate.

A solution of this free base (1.10 g, 2.64 mmole) in hot acetonitrile (5 ml) was added to a solution of (−) dibenzoyltartaric acid.$H_2O$ (0.90 g, 2.4 mmole, prepared from natural tartaric acid) in hot acetonitrile (5 ml). The resulting solution was warmed to dissolve an oil that formed and then allowed to cool slowly with seeding from material obtained earlier in a similar experiment.

The next day, crystalline solid was collected, washed with fresh acetonitrile (5 ml) and dried at 55° under vacuum, giving the resolved salt (0.92 g), m.p. 157-158°. The resolved salt prepared from (−) dibenzoyl-tartaric acid was converted back to free base and then into the HCl salt of the title compound, m.p. 222-223°; $[\alpha]_D^{25}$ +63.0° +0.8° (c=1.0, EtOH).

B. (-) trans-3,4-Dichloro-N-methyl-N-[2-(pyrrolidin-hydronaphth-1-yl)-1,2,3,4-tetra]benzeneacetamide and its hydrochloride salt The mother liquors from the crystallization described in A were treate with excess aqueous $K_2CO_3$, and the free base thus obtained was treated with (+) dibenzoyltartaric acid.$H_2O$ (made from unnatural tartaric acid) giving the enantiomaric salt (0.616 g), m.p. 157-158°. This salt was converted to free base and then into the HCl salt of the title compound, m.p. 21-222°, $[\alpha]_D^{25}$ −63.6° (C=1.0, EtOH).

EXAMPLE 6 trans-3,4-Dichloro N-methyl-N-[2,3-dihydro-2-(pyrrolidin-1-yl)-1H-inden-1-yl]benzeneacetamide hydrochloride Step 1: trans-2,3-Dihydro-2-hydroxy-1-(pyrrolidin-1-yl)-1H-indene 1,2-Epoxy-2,3-dihydro-1-H indene, prepared from indene (34.2 g) according to the procedure of M. Imuta and H. Ziffer, J. Orq. Chem., 44, 1351 (1979), was treated immediately exothermic reaction mixture was set aside for 15 minutes and then evaporated to remove the excess pyrrolidine under reduced pressure The residue was distilled under vacuum to yield trans-2,3-dihydro-2-hydroxy-1-(pyrrolidin-1-yl)-1H-indene (10.2 g), b.p. 148-150°/0.25 torr.

Step 2: trans-2,3-Dihydro-1-methylamino-2-(pyrrolidin-1-Yl)-1H-indene

A solution of methanesulfonyl chloride (6 g) in methylene chloride (50 ml) was added dropwise rapidly to a stirred and cooled (0-5°) solution of trans-2,3-dihydro-2-hydroxy-(pyrrolidin-I-yl)-1H-indene (5.5 g) and triethylamine (6 ml) in methylene chloride (200 ml). After the addition was complete, the mixture was stirred at room temperature for 3 hours and then evaporated under reduced pressure. The residue was treated with a 33% solution of methylamine in ethanol (100 ml) and the mixture was stirred at reflux for 3 hours and evaporated under reduced pressure. The residue was treated with water and extracted twice with ether. The combined ether extracts were washed successively with 2 N sodium hydroxide solution and water, dried over magnesium sulfate and evaporated under reduced pressure to yield a liquid which was distilled under vacuum to give trans-2,3-dihydro-1-methylamino-2-(pyrrolidin-1-yl)-1H-indene (6.3 g) b.p. 118-120°/0.25 torr.

Step 3: trans-3,4-Dichloro-N-methyl-N-[2,3-dihydro-2-(pyrrolidin-1-yl)-1H-inden-1-yl]benzeneacetamide hydrochloride A solution of the above product (5.4 g) in anhydrous tetrahydrofuran (25 ml) was added in one lot to a stirred mixture of 3,4-dichlorophenylacetic acid (5.2 g), dicyclohexylcarbodiimide (5.2 g) and a few milligrams of 4-dimethylaminopyridine in anhydrous tetrahydrofuran (50 ml). The mixture was stirred at room temperature overnight and filtered. The solid was washed with a small quantity of anhydrous tetrahydrofuran and the combined filtrates were evaporated under reduced pressure. The residue was dissolved in anhydrous ether (50 ml) and the solution was filtered to remove a small quantity of insoluble material. The clear filtrate was added to an excess of an etheral solution of gaseous hydrogen chloride. The sticky hydrochloride that separated was removed by decantation and crushed under anhydrous ether to a fine powder which was boiled with acetonitrile (50 ml) briefly and cooled to yield a colorless crystalline material which was filtered, washed with ether, and air-dried to give the title compound (6.1 g), m.p. 233–235°.

EXAMPLE 7 trans-3,4-Dichloro-N-methyl-N-[3,4-dihydro-3-(pyrrolidin-1-yl)-2H-benzopyran-4-yl]benzeneacetamide and its hydrochloride salt Step 1: Benzopyran A mixture of 4-chromanol (30 g; 0.02 mole), benzene (200 ml) and 4-toluenesulfonic acid (200 mg) was refluxed, with a Dean-Stark trap, until separation of water ceased (ca. 3 hrs.). It was then washed successively with saturated $NaHCO_3$ aqueous solution and water, dried over anhydrous $MgSO_4$ and evaporated under reduced pressure to yield an almost colorless liquid which was distilled under vacuum to give benzopyran (20.2 g, 76.4%) b.p. 73–78°/3 torr.

Step 2: 3,4-Dihydro-4-methylamino-3-(1-pyrrolidin)-2H-1-benzopyran

3-Chloroperoxybenzoic acid lMCPBA, 19.0 g of 80–85%; ca. 0.09 mole) was added in small portions to a vigorously stirred mixture of a solution of 11.4 g (0.087 mole) of the above product in $CH_2Cl_2$ (300 ml) and saturated aqueous $NaHCO_3$ (300 ml) at 0–5°. After the addition was complete, the mixture was stirred for 3 hours at 0–5° and additional MCPBA (5 g) was added in small portions. The mixture was then stirred for 1 hour at 0–5° and the methylene chloride layer separated, was washed successively with cold saturated aqueous $NaHCO_3$, cold 10% aqueous sodium sulfite and water, dried over anhydrous $MgSO_4$ and filtered. The filtrate was treated with pyrrolidine (25 ml) and the mixture was evaporated under reduced pressure. The residue was treated with an additional amount of pyrrolidine (10 ml), warmed briefly to ca. 80° and evaporated under reduced pressure. The residue was dissolved in ether and extracted with 1 N HCl (200 ml). The acid fraction was extracted once with ether and the ether extract was discarded. The aqueous layer was cooled and basified carefully with 20% aqueous NaOH. The mixture was then extracted with ether (2X) and the combined ether extracts were washed with water, dried over $MgSO_4$ and evaporated under reduced pressure to yield a reddish brown liquid (9.3 g, 48.9%) which was used as such in the next reaction.

A solution of methanesulfonyl chloride (5.2 g; 0.045 mole) in methylene chloride (25 ml) was added dropwise to a stirred and cooled solution of the above product (9.3 g; 0.042 mole) and triethylamine (9 g; 0.09 mole) in methylene chloride (200 ml). After the addition was complete, the mixture was stirred at room temperature for 3 hours and then evaporated at reduced pressure. The residue was treated with a 33% solution of methylamine in ethanol (100 ml) and the mixture was stirred at reflux for 3 hours and evaporated under reduced pressure. The residue was treated with water and extracted with ether (2 X). The ether extract was washed successively with 2 N NaOH and water, dried over anhyd. $MgSO_4$ and evaporated under reduced pressure to yield a viscous, reddish brown liquid, 3,4-dihydro-4-methylamino-3-(1-pyrrolidin)-2H-1-benzopyran (8.2 g; 84%) which was used as such in the following step.

Step 3: Trans-3,4-Dichloro-N-methyl-N-3,4-dihydro-3-(pyrrolidin-1-yl)-2H-benzopyran-4-yl]benzeneacetamide and its hydrochloride salt A solution of the above benzopyran (8.1 g) and triethylamine (6 g) in methylene chloride (200 ml) was stirred and treated with a solution of 3,4-dichlorophenylacetyl chloride (8.5 g) in methylene chloride (10 ml). After the addition was complete, the mixture was stirred at room temperature for 2 hours and then treated with a 2% aqueous solution of sodium hydroxide (150 ml). The mixture was transferred to a separatory funnel, shaken vigorously and the methylene chloride layer was separated, washed successively with saturated aqueous sodium bicarbonate solution and water, dried over magnesium sulfate and evaporated under reduced pressure. The residual viscous liquid was dissolved in anhydrous ether and the solution was added to an excess of an etheral solution of gaseous hydrogen chloride. The lumpy hydrochloride that separated was removed by decantation, crushed to a fine powder under anhydrous ether and filtered. The product was boiled with acetonitrile (100 ml) and filtered to remove slight coloration. The colorless solid thus obtained was recrystallized from a mixture of methanol and ether to yield the title compound, m.p. 260–261° (dec.).

EXAMPLE 8 trans-3,4-Dichloro-N-methyl-N-[(3-(pyrrolidin-1-yl)-1,2,3,4-tetrahydronaphthalen-2-yl)]benzamide The starting diamine prepared in Example 2, step 2 (1.0 g) was suspended in dry methylene chloride (20 ml) and cooled in an ice-water bath. While stirring, a solution of 3,4-dichlorobenzoyl chloride (1.35 g) in methylene chloride (10 ml) was added dropwise. The resulting mixture was allowed to warm to room temperature, stirred overnight, quenched with half-saturated aqueous $Na_2CO_3$, and extracted with methylene chloride. The combined extracts were washed with brine, dried and evaporated to give a brownish oil. The crude oil was chromatographed by flash column chromatography (silica gel; methylene chloride: methanol = 30:1) to give the desired amide (1.1 g), m.p. 126–129° from acetone-hexane.

EXAMPLE 9 trans-3,4-Dichloro-N-methyl-N-[3-(pyrrolidin-1-yl)-1,2,3,4-tetrahydronaphthalen-2-yl)benzeneacetamide 2-naphthalenesulfonic acid salt Step 1: 2,3-Epoxy-1,2,3,4-tetrahydronaphth 1,4-Dihydronaphthalene (5 g) was dissolved in methylene chloride (250 ml) and saturated aqueous $NaHCO_3$ (280 ml). The mixture was stirred vigorously at room temperature while mata-chloroperbenzoic acid (70%, 10.0 g) was added in portions. After 1 hour, an aqueous solution of $Na_2S_2O_3$ (1M, 100 ml) and methylene chloride were added. The methylene chloride layer was separated, washed with water and brine, dried (MgSO4) and evaporated to give a brownish crude mixture, which was chromatographed on a flash column (silica gel; ether: hexane = 1:6) to give 2,3-epoxy-1,2,3,4-tetrahydronaphtbalene (3.45 g)

Step 2: trans-2-Hydroxy-3-(pyrrolidin-1-yl)-1,2,3,4-tetrahydronaphth

The above product (3.45 g), pyrrolidine (2.8 g) and dioxane (15 ml) were sealed under vacuum in a glass tube. The sealed tube was heated at 100° for 15 hours. The content was evaporated under reduced pressure and the residue was partitioned between ether (50 ml) and 1 N HCl (50 ml). The aqueous layer was separated, basified to pH9, and extracted with methylene chloride. The combined extracts were washed with brine, dried, and evaporated to give trans-2-hydroxy-3-(pyrrolidin-1-yl)-1,2,3,4-tetrahydro-naphthalene (4.5 g).

Step 3: trans-2-MethYlamino-3-(pyrrolidin-1-yl)-1,2,3,4-tetrahydronaphth

The above product (4.5 g) and triethylamine (3.5 ml) were dissolved in methylene chloride (80 ml) and stirred at 0°, while a solution of methanesulfonyl chloride (1.83 ml) in $CH_2Cl_2$ (40 ml) was added dropwise. After the addition, the mixture was placed in the refrigerator overnight. Water (50 ml) was added, and the organic layer was separated, washed with brine, dried ($MgSO_4$) and evaporated to give a brownish residue. The residue was dissolved in 33% $CH_3NH_2$/ethanol (20 ml) and stirred at reflux under $N_2$ for 2 hours. The excess $CH_3NH_2$ and ethanol were evaporated. The residue was dissolved in methylene chloride (100 ml) and washed with water and brine. Evaporation gave trans-2-methylamino-3-pyrrolidin-1-yl)-1,2,3,4-tetrahydronaphth (4.2 g).

Step 4: Trans-3,4-Dichloro-N-methyl-N-3-(pyrrolidin-1-yl)-1,2,3,4-tetrahydronaphthalen-2-yl)benzeneacetamide 3,4-Dichlorophenylacetic acid (1.05 g) and carbonyldiimidazole (856 mg) were dissolved in dry THF (20 ml). This solution was cannulated into a stirred suspension of the above product (1.0 g) in methylene chloride (20 ml) at 0°. The mixture was allowed to warm to room temperature and stirred overnight. Water (50 ml) and methylene chloride (100 ml) were added and the organic layer was separated, washed with brine, dried, and evaporated to give a crude product which was chromatographed (silica gel; $CH_2Cl_2$: $CH_3OH=40:1$) to yield the pure free base of the title compound (1.2 g). Its naphthalenesulfonate was recrystallized from ethyl acetate: 2-propanol; m.p. 161-164°.

The compounds prepared in Examples 1-9 and other compounds which were prepared or can be prepared by the methods described in the specification are listed in Tables I and II.

TABLE I

| Ex. No. | A | B | C | D | n | R | R¹ | R² | R³ | X | Y | salt | m.p. °C |
|---|---|---|---|---|---|---|---|---|---|---|---|---|---|
| 1 | CH₂ | 5-OCH₃ | H | H | 1 | CH₃ | CH₃ | —(CH₂)₄— | H | 3-Cl | 4-Cl | HCl | 230-2 |
| 1A | CH₂ | 5-OCH₃ | H | H | 1 | CH₃ | CH₃ | —(CH₂)₄— | H | 3-Cl | 4-Cl | HCl | 203-5 (+) isomer |
| 2 | CH₂ | H | H | H | 1 | CH₃ | CH₃ | —(CH₂)₄— | H | 3-Cl | 4-Cl | HCl | 232-4 |
| 3 | CH₂ | 6-OCH₃ | H | H | 1 | CH₃ | CH₃ | —(CH₂)₄— | H | 3-Cl | 4-Cl | HCl | 245-7 (dec) |
| 4 | CH₂ | 6-OH | H | H | 1 | CH₃ | CH₃ | —(CH₂)₄— | H | 3-Cl | 4-Cl | HCl | 238-40 |
| 5A | CH₂ | H | H | H | 1 | CH₃ | CH₃ | —(CH₂)₄— | H | 3-Cl | 4-Cl | HCl | 222-3 (+) isomer |
| 5B | CH₂ | H | H | H | 1 | CH₃ | CH₃ | —(CH₂)₄— | H | 3-Cl | 4-Cl | HCl | 221-2 (−) isomer |
| 6 | O | H | H | H | 0 | CH₃ | CH₃ | —(CH₂)₄— | H | 3-Cl | 4-Cl | HCl | 233-5 |
| 7 | O | H | H | H | 1 | CH₃ | CH₃ | —(CH₂)₄— | H | 3-Cl | 4-Cl | HCl | 260-1 (dec) |
| 10 | CH₂ | H | H | H | 1 | CH₃ | CH₃ | —(CH₂)₄— | H | H | 4-Br | HCl | 168-70 |
| 11 | CH₂ | H | H | H | 1 | CH₃ | CH₃ | —(CH₂)₄— | H | H | H | HCl | 178-80 |
| 12 | CH₂ | H | H | H | 1 | CH₃ | CH₃ | —(CH₂)₄— | H | H | 4-CF₃ | HCl | 170-2 |
| 13 | CH₂ | 5-OCH₃ | H | H | 1 | CH₃ | CH₃ | —(CH₂)₄— | H | 3-Cl | 4-Cl | CH₃SO₃H | 193-5 |
| 14 | CH₂ | 5-OH | H | H | 1 | CH₃ | CH₃ | —(CH₂)₄— | H | 3-Cl | 4-Cl | HCl | 273-5 (dec) |
| 15 | CH₂ | 5-OCOC₂H₅ | H | H | 1 | CH₃ | CH₃ | —(CH₂)₄— | H | 3-Cl | 4-Cl | HCl | 228-30 |
| 16 | CH₂ | 5-OCOC₆H₅ | H | H | 1 | CH₃ | CH₃ | —(CH₂)₄— | H | 3-Cl | 4-Cl | HCl | 260-2 |
| 17 | CH₂ | 6-OCH₃ | 7-OCH₃ | H | 1 | CH₃ | CH₃ | —(CH₂)₄— | H | 3-Cl | 4-Cl | HCl | 128-30 (dec) |
| 18 | CH₂ | 6-OH | 7-OCH₃ | H | 1 | CH₃ | CH₃ | —(CH₂)₄— | H | 3-Cl | 4-Cl | HCl | 243-5 |
| 19 | O | H | H | H | 1 | CH₃ | CH₃ | —(CH₂)₄— | H | H | H | HCl | 260-1 (dec) |
| 20 | O | 5-OCH₃ | H | H | 1 | CH₃ | CH₃ | —(CH₂)₄— | H | 3-Cl | 4-Cl | HCl | 205-7 |
| 21 | CH₂ | 5-OCH₂—CH₂OCH₃ | H | H | 1 | CH₃ | CH₃ | —(CH₂)₄— | H | 3-Cl | 4-Cl | HCl | 232-4 |
| 22 | CH₂ | 5-OCH₃ | 6-OCH₃ | H | 1 | CH₃ | CH₃ | —(CH₂)₄— | H | 3-Cl | 4-Cl | HCl | 201-4 |
| 23 | CH₂ | 5-CH₂OCH₃ | 6-OCH₃ | H | 1 | CH₃ | CH₃ | —(CH₂)₄— | H | 3-Cl | 4-Cl | HCl | |
| 24 | CH₂ | 5-OCH₃ | 8-OCH₃ | H | 1 | CH₃ | CH₃ | —(CH₂)₄— | H | 3-Cl | 4-Cl | HCl | 139-141 |
| 25 | CH₂ | 5-CH₂OCH₃ | 6-OH | H | 1 | CH₃ | CH₃ | —(CH₂)₄— | H | 3-Cl | 4-Cl | HCl | 203-7 (dec) |
| 26 | CH₂ | 5-OCH₃ | 7-OCH₃ | H | 1 | CH₃ | CH₃ | —(CH₂)₄— | H | 3-Cl | 4-Cl | HCl | |

TABLE I-continued

| Ex. No. | A | B | C | D | n | R | R¹ | R² | R³ | X | Y | salt | m.p. °C |
|---|---|---|---|---|---|---|---|---|---|---|---|---|---|
| 27 | CH₃ | 5-SCH₃ | 8-OCH₃ | H | 1 | CH₃ | CH₃ | —(CH₂)₄— | H | 3-Cl | 4-Cl | HCl | |
| 28 | CH₂ | 5-CO₂ET | 6-OCH₃ | H | 1 | CH₃ | CH₃ | —(CH₂)₄— | H | 3-Cl | 4-Cl | HCl | |
| 29 | CH₂OH | H | H | H | 1 | CH₃ | CH₃ | —(CH₂)₄— | CH₂OH | 3-Cl | 4-Cl | HCl | |
| 30 | CHCH₂OH | 5-NH₂ | 6-OCH₃ | H | 1 | CH₃ | CH₃ | —(CH₂)₄— | H | 3-Cl | 4-Cl | HCl | |
| 31 | CHCH₂OH | 6-OCH₃ | H | H | 1 | CH₃ | CH₃ | —(CH₂)₄— | H | 3-Cl | 4-Cl | HCl | |
| 32 | CH₂ | 5-CH₂CO₂C₃H₇ | 6-OH | H | 1 | CH₃ | CH₃ | —(CH₂)₄— | H | 3-Cl | 4-Cl | HCl | |
| 33 | CH₂ | 5-N(CH₃)₂ | 6-OH | H | 1 | CH₃ | CH₃ | —(CH₂)₄— | H | 3-Cl | 4-Cl | HCl | |
| 34 | CHCON(Et)₂ | 6-OCH₃ | H | H | 1 | CH₃ | CH₃ | —(CH₂)₄— | H | 3-Cl | 4-Cl | HCl | |
| 35 | S | 5-OCH₃ | 6-OCH₃ | 7-OCH₃ | 1 | C₂H₅ | C₂H₅ | —(CH₂)₃— | H | H | 4-CF₃ | NSA* | |
| 36 | O | 4-N(C₃H₇)CH₃ | H | H | 1 | C₃H₇ | CH₃ | CH₂C₆H₅ | H | 3-NO₂ | 4-SO₂CF₃ | HCl | |
| 37 | CH₂ | 6-OC₃H₇ | H | H | 1 | C₂H₅ | CH₃ | (CH₂)₂CH(OH)CH₂— | H | 3-F | 4-F | HCl | |
| 38 | — | 4-NH₂ | 5-F | 6-F | 0 | CH₃ | CH₃ | —(CH₂)₂O(CH₂)₂— | H | H | 4-SO₂CH₃ | HBr | |
| 39 | — | 4-OCH₃ | H | H | 0 | CH₃ | CH₃ | —(CH₂)₄— | H | 3-Cl | 4-Cl | HCl | |
| 40 | — | 4-CH₂SC₂H₅ | 5-OH | H | 0 | CH₃ | CH₃ | CH₂—I | H | 3-Cl | 4-NO₂ | HCl | |
| 41 | CH₂ | 5-OC₃H₇ | 6-BH | H | 1 | CH₃ | CH₃ | CH₂— | H | 3-F | 4- | HBr | |
| 42 | CH₂ | 6-Cl | 7-Cl | H | 1 | CH₃ | CH₃ | —(CH₂)₂NCH₃(CH₂)₂— | CO—C₃H₇ | SO₂CH₃ 2-OCH₃ | 4-NO₂ | — H₂SO₄ | |
| 43 | CH₂ | 5-NMe₂ | 6-CH₃ | 8-Cl | 1 | CH₃ | H | 3-ABHX* | CHO | 3-Cl | 4-CN | H₂SO₄ | |
| 44 | CH₂ | 5-SC₂H₅ | 6-Cl | H | 1 | CH₃ | CH₃ | 3-ABHP* | CH₃ | 3-Cl | 4-OCH₃ | HCl | |
| 45 | CH₂ | 6-SH | H | H | 1 | CH₃ | C₂H₅ | CH₂CH₂C₆H₅ | H | 3-Cl | 4-OCH₃ | HCl | |
| 46 | CH(CH₃) | H | H | H | 1 | C₃H₇ | CH₃ | —(CH₂)₄— | H | 2-Cl | 3-Cl | HCl | |
| 47 | CH(C₃H₇) | H | H | H | 1 | C₃H₇ | CH₃ | —(CH₂)₃— | H | 2-Cl | 4-Cl | HCl | |
| 48 | CH₂ | 5-OCH₂OCH₃ | H | H | 1 | CH₃ | CH₃ | —(CH₂)₄— | H | 3-Cl | 4-Cl | HCl | |
| 49 | CH₂ | 7-OH | H | H | 1 | CH₃ | CH₃ | —(CH₂)₄— | H | 3-Cl | 4-Cl | HCl | |
| 50 | CH₂ | 5-OCH₃ | H | H | 1 | CH₃ | CH₃ | —CH₂CH=CHCH₂— | H | 3-Cl | 4-OCH₃ | HCl | |
| 51 | CHCO₂H | H | H | H | 1 | CH₃ | CH₃ | —(CH₂)₄— | H | 3-NO₂ | 4-OCH₃ | HCl | |
| 52 | CHCO₂CH₃ | H | H | H | 1 | CH₃ | CH₃ | —(CH₂)₄— | H | 2-CN | 5-NO₂ | HCl | |
| 53 | CHCON(C₃H₇)₂ | H | H | H | 1 | CH₃ | CH₃ | —(CH₂)₄— | H | 3-Cl | 4-Cl | HCl | |
| 54 | CH₂ | H | H | H | 1 | H | CH₃ | H | H | 3-Cl | 4-Cl | HCl | |
| 55 | CHCHO | H | H | H | 1 | C₃H₇ | CH₃ | CH₂CF₃ | H | 3-Cl | 4-Cl | HCl | |
| 56 | CHCO₂CH₃ | H | H | H | 1 | H | CH₃ | CH₃C₂H₅OH | H | 3-Cl | 4-Cl | HCl | 193-6 (dec) |

TABLE I-continued

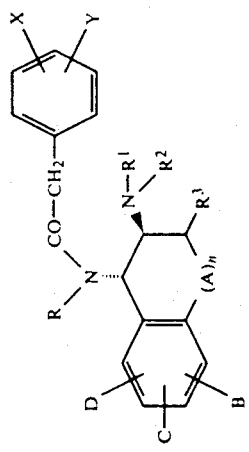

| Ex. No. | A | B | C | D | n | R | R¹ | R² | R³ | X | Y | salt | m.p. °C. |
|---|---|---|---|---|---|---|---|---|---|---|---|---|---|
| 57 | CHCON— (CH₂)₂ | H | H | H | 1 | H | H | —(CH₂)₅— | H | 3-Cl | 4-Cl | HCl | |
| 58 | CH₂ | 6-OCH₃ | H | H | 1 | CH₃ | H | —CH₂CH=CHCH₂— | H | 3-Cl | 4-Cl | HCl | |
| 59 | CH₂ | 4-CH₂OC₃H₇ | 5-Cl | H | 1 | H | H | —(CH₂)₄— | CH₃ | 3-I | 4-Br | HCl | |
| 60 | CH₂ | 5-CH₂CONHCH₃ | H | H | 1 | H | H | —(CH₂)₄— | H | H | 3-Cl | HCl | |
| 61 | CH₂ | 6-CH₂CO₂H | 7-CH₃ | H | 1 | CH₃ | H | —(CH₂)₃— | H | 3-Cl | 3-Cl | HCl | |
| 62 | CH₂ | 4-CH₂COC₂H₅ | H | H | 1 | H | H | —(CH₂)₃— | H | 3-Cl | 4-Br | HCl | |
| 63 | CH₂ | 5-CH₂CHO | 6-C₂H₅ | H | 1 | H | H | —(CH₂)₃— | H | 3-NO₂ | 4-OMe | HCl | |
| 64 | CH₂ | 4-Br | 5-I | H | 1 | H | H | —(CH₂)₅— | H | 2-Cl | 3-Br | HCl | |
| 65 | CH₂ | 5-SC₃H₇ | 6-NH₂ | H | 1 | H | CH₃ | —(CH₂)₄— | H | 3-Cl | 4-OMe | HCl | |
| 66 | CH₂ | 4-SCH₃ | 5-N(C₂H₅)₂ | H | 1 | H | H | —(CH₂)₄— | H | 3-Cl | 4-Cl | HCl | |
| 67 | CH₂ | 5-Br | 6-Cl | 7-I | 1 | H | H | —(CH₂)₄— | H | 3-Cl | 4-Cl | HCl | |
| 68 | CH₂ | 5-OC(S)N(CH₃)₂ | H | H | 1 | CH₃ | H | —(CH₂)₄— | H | 3-Cl | 4-Cl | HCl | 255-7 |
| 69 | CH₂ | H | 7,8-(—CH=CH—CH=CH—) | | 1 | CH₃ | H | —(CH₂)₄— | H | 3-Cl | 4-Cl | HCl | 280-2 (dec) |
| 70 | CH₂ | H | 6,7-(—CH=CH—CH=CH—) | | 1 | CH₃ | H | —(CH₂)₄— | H | 3-Cl | 4-Cl | HCl | |
| 71 | CH₂ | H | 5,6-(—CH=CH—CH=CH—) | | 1 | CH₃ | H | —(CH₂)₄— | H | 2,3-(—CH=CH—S—) | | HCl | 242-5 (dec) |
| 72 | CH₂ | 5-OCH₃ | H | H | 1 | CH₃ | H | —(CH₂)₄— | H | H | 4-NO₂ | HCl | |
| 73 | CH₂ | H | H | H | 0 | CH₃ | —(CH₂)₂CH(CH₃)(CH₂)₂— | | CH₂OH | 3-Cl | 4-Cl | HCl | |
| 74 | — | H | 8-OCH₃ | H | 0 | CH₃ | —(CH₂)₂CH(OH)CH₂— | | H | 3-Cl | 4-Cl | HCl | |
| 75 | CH₂ | 5-OCH₃ | 6-OH | 7-OH | 1 | C₂H₅ | H | —(CH₂)₃— | H | H | 4-SO₂C₃H₇ | HCl | |
| 76 | CH₂ | 5-CH₃ | 5,6-(—CH=CH—CH=CH—) | | 1 | CH₃ | H | —(CH₂)₄— | H | 3-Cl | 4-Cl | HCl | |
| 77 | CH₂ | H | 6,7-(—CH=CH—CH=CH—) | | 1 | CH₃ | H | —(CH₂)₃— | H | 3-Cl | 4-Cl | HCl | |
| 78 | CH₂ | H | 7,8-(—CH=CH—CH=CH—) | | 1 | CH₃ | H | —(CH₂)₄— | H | 3-Cl | 4-Cl | HCl | |
| 79 | CH₂ | H | H | H | 1 | CH₃ | H | —(CH₂)₄— | H | 3-Cl | 4-Cl | HCl | |

TABLE II

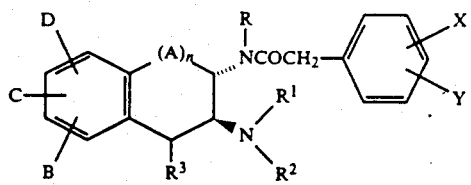

| Ex. No. | A | B | C | D | n | R | R¹ | R² | R³ | X | Y | salt | m.p. °C. |
|---|---|---|---|---|---|---|---|---|---|---|---|---|---|
| 8 | $CH_2$ | H | H | H | 1 | $CH_3$ | —$(CH_2)_4$— | | H | 3-Cl | 4-Cl | (base) | 126-9 |
| 9 | $CH_2$ | H | H | H | 1 | $CH_3$ | —$(CH_2)_4$— | | H | 3-Cl | 4-Cl | NSA* | 161-4 |
| 80 | — | H | H | H | 0 | $CH_3$ | —$(CH_2)_2CH(CH_3)(CH_2)_2$— | | $CH_2OH$ | H | 4-$NO_2$ | HCl | |
| 81 | $CH_2$ | 5-OH | H | H | 0 | $CH_3$ | —$(CH_2)_2CH(OH)CH_2$— | | H | 3-Cl | 4-Cl | HCl | |
| 82 | $CH_2$ | 5-$OCH_3$ | 8-$OCH_3$ | H | 1 | $C_2H_5$ | —$(CH_2)_4$— | | H | 3-Cl | 4-Cl | HCl | |
| 83 | $CH_2$ | 5-$CH_3$ | 6-OH | 7-OH | 1 | $CH_3$ | —$(CH_2)_3$— | | H | H | 4-$SO_2C_3H_7$ | HCl | |

*NSA = 2-naphthalenesulfonic acid

Analgesia Testing Procedure

The standard procedure for detecting and comparing the analgesic activity of compounds is the phenylquinone writhing test (PQW) modified from E. Seigmund, et al.; *Proc. Soc. Exp. Biol. Med.*, 95, 729 (1957).

Test compounds were dissolved in saline or distilled water using dilute lactic acid as needed, or suspended in an aqueous vehicle containing 2% by volume of Tween 80®, a pharmacological dispersant manufactured by Fisher-Scientific Company and containing 100% polysorbate 80, and 0.25% by weight of Methocel®A15C powder, a suspending agent manufactured by Dow Chemical company and containing 100% methylcellulose. Test compounds were given orally or subcutaneously to fasted (17-21 hrs) male white mice (CF1), 5-15 animals per graded dose, in a volume of 10 ml/kg body weight. After 5-25 minutes, aqueous 0.01% phenyl-p-benzoquinone, 0.125 mg/kg, was injected intraperitoneally. After an additional 5 minutes, mice were observed 10 minutes for the characteristic stretching or writhing syndrome which is indicative of pain produced by phenylquinone. The effective analgesic dose in 50% of the mice (ED50) was calculated by the moving average method of W.R. Thompson, *Bac. ReV.*, 11, 115-145 (1947).

The mouse analgesic data are summarized in Table III.

TABLE III

| Ex. No. | Analgesic Activity in Mice ED50 (mg/kg) | |
|---|---|---|
| | s.c. | p.o. |
| 1 | 0.46 | 6.5 |
| 1A | 0.15 | 5.2 |
| 2 | 2.7 | 13. |
| 3 | 1.5 | 6.5 |
| 4 | 0.032 | 4.2 |
| 5A | 0.90 | 3.4 |
| 5B | >81. | >81. |
| 6 | 1.5 | 30. |
| 7 | 1.7 | 36 |
| 8 | 16. | 47. |
| 9 | 47. | >81. |
| 10 | 8.1 | 54. |
| 11 | 30. | >81. |
| 12 | 19. | 54. |
| 13 | 0.33 | 7.4 |
| 14 | 0.72 | 13. |
| 15 | 0.24 | 10. |
| 16 | 0.71 | 10. |
| 18 | 0.19 | 3.3 |
| 19 | 1.7 | 36. |

TABLE III-continued

| Ex. No. | Analgesic Activity in Mice ED50 (mg/kg) | |
|---|---|---|
| | s.c. | p.o. |
| 20 | 1.2 | 30. |
| 22 | 8.1 | 16. |
| 24 | 47. | 24. |
| 25 | 0.19 | 54. |
| 48 | 4.5 | 13. |
| 49 | 0.46 | 16. |
| 50 | 0.24 | 3.4 |
| 68 | 1.7 | 18. |
| 69 | 3.0 | 16. |
| 72 | 0.46 | 16. |
| U-50, 488H | 1.2 | 13. |
| Morphine | 1.0 | 3.8 |

As shown in Table III, compounds of the invention produce potent analgesic effects in warm-blooded animals. This analgesia is in the same range of potency as morphine and of the standard kappa agonist analgesic U-50,488H [P.F. VonVoigtlander, et al.; *J. Pharmacol. Exp. Ther.*, 244, 7 (1983)].

Strong sedation, occurring at ≧3x the analgesic ED50 dose, was an additional property observed with all compounds of the invention when tested in mice. This sedation is characteristic of kappa agonist compounds such as U-50,488H [P.F. VonVoigtlander, et al.; *J. Pharmacol. Exp. Ther.*, 224, 7 (1983)]. Morphine and other mu agonist compounds do not produce sedation in mice. All compounds of the invention which produced analgesia in mice (Table III) also produced strong sedation within their analgesically-effective range of doses, suggesting that they have selective kappa agonist activity.

A standard procedure useful for confirming kappa receptor opioid activity is the production of diuresis in the rat. Known kappa agonists such as U-50,488H produce significant increases in urine flow [P.F. VonVoigtlander, et al.; *J. Pharmacol. Exp. Ther.*, 244, 7 (1983)]. Mu agonist analgesics, such as morphine, are largely devoid of this property. Thus, kappa agonist induced urine formation is the basis of a test in rats for distinguishing kappa and mu agonist activity.

Testing for diuretic activity was conducted in male Sprague Dawley rats, weight approximately 200-300 g. Ratss were not fasted prior to use, but no food or water was available for the duration of the study. Animals were allowed to acclimate for approximately 30 minutes in individual metabolism cages, then administered test compound doses subcutaneously in a volume of 1 ml/kg body weight. Spontaneously voided urine was collected for the next five hours. Test compounds were prepared in either distilled water (solutions) or Mehtocel®/Tween 80® suspensions, according to the methods indicated above.

The rat diuretic data are summarized in Table IV.

TABLE IV

KAPPA AGONIST-INDUCED DIURESIS IN RATS
(N = 5 RATS/DOSE)

| EX. NO. | DOSE (mg/kg s.c.) | MEAN CUMULATIVE URINE OUTPUT AT 5 HOURS (ml) | % INCREASE OVER CONTROL |
|---|---|---|---|
| 1 | 0.0 | 0.80 | — |
|  | 0.063 | 1.20 (NS) | 50% |
|  | 0.25 | 3.44* | 330%* |
|  | 1. | 8.76* | 995%* |
|  | 4. | 10.9* | 1263%* |
|  | 16. | 8.64* | 980%* |
| 2 | 0.0 | 1.40 | — |
|  | 0.33 | 0.96 (NS) | −31% |
|  | 1. | 2.24 (NS) | 60% |
|  | 3. | 3.08* | 120%* |
|  | 9. | 6.36* | 354%* |
|  | 27. | 8.56* | 511%* |
| U-50, 488H | 0.0 | 2.44 | — |
|  | 0.063 | 3.48 (NS) | 43% |
|  | 0.25 | 2.84* | 16% |
|  | 1. | 5.44* | 123%* |
|  | 4. | 10.5* | 330%* |
|  | 16. | 13.6* | 457%* |
| MORPHINE | 0.0 | 0.93 | — |
|  | 0.1 | 1.38 (NS) | 48% |
|  | 1. | 2.41* | 159%* |
|  | 20. | Toxic (2/8 dead) | — |

(NS) = not significant
* = P <0.05 significant compared to vehicle control

As shown in Table IV, compounds of the invention produced large increases in urine flow similar to that observed with the standard kappa agonist analgesic U-50,488H. Mu agonist analgesics (morphine) produce minimal or no diuresis in rats. These data confirm that compounds of the invention are kappa agonist analgesics.

Dosage Forms

Dosage forms (compositions) suitable for administration contain from about 0.1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or entericcoated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of the active ingredient, 3 milligrams of magnesium stearate, 75 milligrams of microcrystalline cellulose, 10 milligrams of starch and 112 milligrams of lactose. Appropriate coatings may be applied to increase palatability or delay absorption.

Injectable Composition

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymet-hyl cellulose, 5 milligrams of sodium benzoate, 1.0 grams of sorbitol solution, U.S.P., and 0.025 milliliters of vanillin.

The term "consisting essentially of" as used in the present disclosure is intended to have its customary meaning, namely, that all specified material and conditions are very important in practicing the invention but that unspecified materials and conditions are not excluded so long as they do not prevent the benefits of the invention from being realized.

What is claimed is:

1. A compound having the formula:

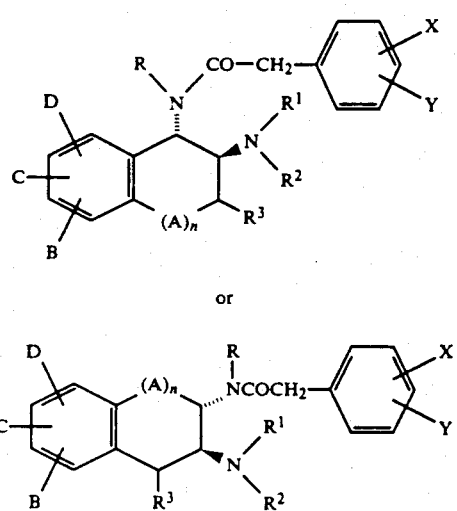

wherein for the enantiomers and racemic mixtures
n is 1
A is —O—, or —S—;
two of B, C and D when on adjacent carbon atoms taken together form a fused benzo ring; and the remaining group is selected from the group consisting of H, OH, $OCOR^5$, $OCH_2CH_2OR^5$, $OR^6$, $R^6$, $CH_2OR^6$, $CH_2COR^7$, Cl, F, Br, I, $NH_2$, $NHR^8$, $NR^8R^9$, SH, $SR^6$, $CH_2SR^6$ and $OC(S)N(CH_3)_2$;
X and Y independently are selected from the group consisting of H, $OCH_3$, Cl, F, Br, I, $NO_2$, $CF_3$, CN, $SO_2R^{10}$, and $SO_2CF_3$ or;
X and Y taken together with the benzene ring form

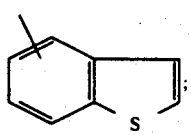

R and $R^1$ independently are selected from the group consisting of H, and alkyl of 1 to 3 carbon atoms;
$R^2$ is H; alkyl of 1 to 6 carbon atoms; CH2CF3; alkenylmethyl of 3 to 6 carbon atoms; hydroxyalkylmethyl of 2 to 5 carbon atoms; cycloalkyl of 3 to 6 carbon atoms; cyclopropylmethyl; cyclobutylmethyl, or phenylalkyl of 7 to 9 carbon atoms; or $R^2$ can be taken together with $R^1$ and the nitrogen to which they are attached to be 1-azetidinyl; 1-pyrrolidinyl optionally substituted at the 3-position by OH, alkyl of 1 to 3 carbon atoms, alkoxy of 1 to 3 carbon atoms or alkanoyloxy of 1 to 3 carbon atoms; 1-piperazinyl optionally substituted at the 4-position by alkyl of 1 to 3 carbon atoms; 1-morpholino; 2,5-dihydro-1H-pyrrol-1-yl; 3-azabicyclo(3.1.0)hexan-3-yl; or 3 azabicyclo(3.2.0)-heptan-3-yl;
$R^3$ is H;
$R^5$ is alkyl of 1 to 6 carbon atoms, phenyl, or monosubstituted phenyl;
$R^6$, $R^8$, $R^9$, $R^{10}$ and $R^{13}$ are independently an alkyl group of 1 to 3 carbon atoms; and
$R^7$ is selected from the group consisting of H, OH, $OR^{13}$, $NHR^{13}$, and $NR_2^{13}$; or a stable N-oxide or a pharmaceutically acceptable salt thereof.

2. The compound of claim 1 wherein the compound is of Formula (I).

3. The compound of claim 2 wherein the compound has the formula

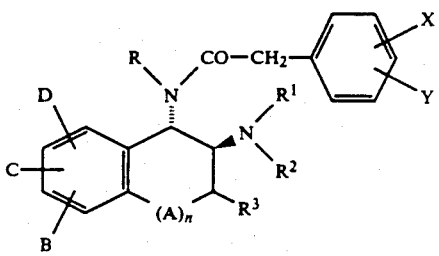

and the definitions of A, B, C, D, n, X, Y, R, $R^1$, $R^2$, and $R^3$ are as in claim 1.

4. The compound of claim 3 wherein B is H, OH, $OCOR^5$, $OCH_2CH_2OR^5$, $OR^6$, $CH_2OR^6$, or $CH_2COR^7$; and C and D form a fused benzo ring at the 5,6 position, the 6,7 position, or the 7,8 position.

5. The compound of claim 3 wherein B is H, OH, or $OR^6$.

6. The compound of claim 3 wherein $R^1$ and $R^2$ are taken together with the nitrogen to which they are attached to form the group 2,5-dihydro-1H-pyrrol-1-yl.

7. The compound of claim 3 wherein
A is O;
B is H or $OR^6$;
C and D form a fused benzo ring at the 5,6 position, the 6,7 position, or the 7,8 position; and
$R^1$ and $R^2$ are taken together with the nitrogen to which they are attached to form the group 2,5-dihydro-1H-pyrrol-1-yl.

8. A pharmaceutical composition consisting essentially of a pharmaceutically acceptable carrier and an effective amount of a compound of claim 1.

9. A pharmaceutical composition consisting essentially of a pharmaceutically acceptable carrier and an effective amount of a compound of claim 2.

10. A pharmaceutical composition consisting essentially of a pharmaceutically acceptable carrier and an effective amount of a compound of claim 3.

11. A pharmaceutical composition consisting essentially of a pharmaceutically acceptable carrier and an effective amount of a compound of claim 4.

12. A pharmaceutical composition consisting essentially of a pharmaceutically acceptable carrier and an effective amount of a compound of claim 5.

13. A pharmaceutical composition consisting essentially of a pharmaceutically acceptable carrier and an effective amount of a compound of claim 6.

14. A pharmaceutical composition consisting essentially of a pharmaceutically acceptable carrier and an effective amount of a compound of claim 7.

15. A method of treating pain in a mammal comprising administering to the mammal an analgesically effective amount of a compound of claim 1.

16. A method of treating pain in a mammal comprising administering to the mammal an analgesically effective amount of a compound of claim 2.

17. A method of treating pain in a mammal comprising administering to the mammal an analgesically effective amount of a compound of claim 3.

18. A method of treating pain in a mammal comprising administering to the mammal an analgesically effective amount of a compound of claim 4.

19. A method of treating pain in a mammal comprising administering to the mammal an analgesically effective amount of a compound of claim 5.

20. A method of treating pain in a mammal comprising administering to the mammal an analgesically effective amount of a compound of claim 6.

21. A method of treating pain in a mammal comprising administering to the mammal an analgesically effective amount of a compound of claim 7.

* * * * *